United States Patent
Hiratsuka et al.

Patent Number: 5,466,663
Date of Patent: Nov. 14, 1995

[54] TETRAHYDROPHTHALIMIDE DERIVATIVES AND THEIR USE AS HERBICIDES

[75] Inventors: Mitsunori Hiratsuka, Oita; Minoru Takano, Kameoka; Masayuki Enomoto, Takarazuka; Satoru Kizawa, Kakogawa; Kazuo Saitoh, Toyonaka, all of Japan

[73] Assignee: Sumitomo Chemical Company, Limited, Osaka, Japan

[21] Appl. No.: 292,189

[22] Filed: Aug. 18, 1994

[30] Foreign Application Priority Data

Aug. 19, 1993 [JP] Japan ................... 5-204961

[51] Int. Cl.$^6$ .................... A01N 43/38; C07D 209/48
[52] U.S. Cl. ................ 504/286; 504/219; 540/602; 548/476; 548/467
[58] Field of Search ................. 504/219, 286; 540/602; 548/467, 476

[56] References Cited

U.S. PATENT DOCUMENTS

| | | | |
|---|---|---|---|
| 4,536,209 | 8/1985 | Jikihara et al. | 548/513 X |
| 4,595,409 | 6/1986 | Haga et al. | 548/513 X |
| 4,684,397 | 8/1987 | Nagano et al. | 548/513 X |
| 4,770,695 | 9/1988 | Nagono et al. | 548/513 X |

FOREIGN PATENT DOCUMENTS

| | | | |
|---|---|---|---|
| 0095192 | 5/1983 | European Pat. Off. | |
| 61-40261 | 2/1986 | Japan | C07D 209/48 |

*Primary Examiner*—Jacqueline Haley
*Attorney, Agent, or Firm*—Birch, Stewart, Kolasch & Birch

[57] ABSTRACT

There is disclosed a compound of the formula:

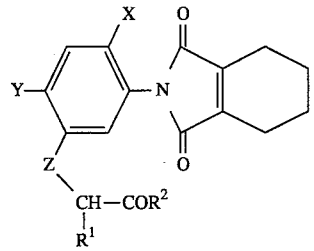

wherein X is hydrogen or halogen; Y is halogen; Z is oxygen or sulfur; $R^1$ is hydrogen or alkyl; and $R^2$ is a group of the formula:

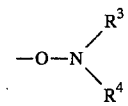

wherein $R^3$ and $R^4$ are the same or different, and each is hydrogen, alkyl, cycloalkyl or benzyl, or the ends of $R^3$ and $R^4$ are connected together to be alkylene; or $R^2$ is a group of the formula:

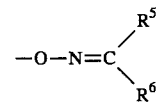

wherein $R^5$ and $R^6$ are the same or different, and each is hydrogen or alkyl, or the ends of $R^5$ and $R^6$ are connected together to be alkylene, with the proviso that $R^2$ is a group of the formula:

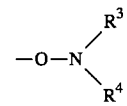

when Z is oxygen, which is useful as a herbicide.

7 Claims, No Drawings

TETRAHYDROPHTHALIMIDE DERIVATIVES AND THEIR USE AS HERBICIDES

The present invention relates to a compound of the formula:

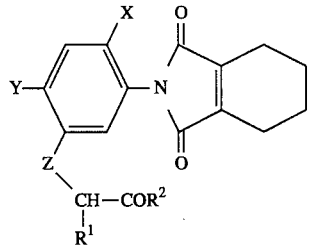

wherein X is hydrogen or halogen; Y is halogen; Z is oxygen or sulfur; $R^1$ is hydrogen or alkyl; and $R^2$ is a group of the formula:

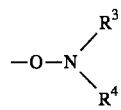

wherein $R^3$ and $R^4$ are the same or different, and each is hydrogen, alkyl, cycloalkyl or benzyl, or the ends of $R^3$ and $R^4$ are connected together to be alkylene; or $R^2$ is a group of the formula:

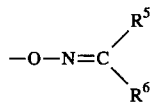

wherein $R^5$ and $R^6$ are the same or different, and each is hydrogen or alkyl, or the ends of $R^5$ and $R^6$ are connected together to be alkylene, with the proviso that $R^2$ is a group of the formula:

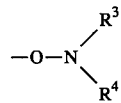

when Z is oxygen.

In the compound [I] of the present invention, X is hydrogen or halogen such as fluorine, chlorine and bromine, preferably hydrogen or fluorine, more preferably, fluorine; Y is halogen such as fluorine, chlorine and bromine; Z is oxygen or sulfur, preferably sulfur; $R^1$ is hydrogen; or $C_1$–$C_4$ alkyl such as methyl, ethyl, propyl and butyl; $R^3$ and $R^4$ are the same or different, and each is hydrogen, $C_1$–$C_6$ alkyl such as methyl, ethyl, propyl and butyl, preferably methyl or ethyl, $C_3$–$C_7$ cycloalkyl such as cyclopropyl and cyclohexyl, or benzyl; or the ends of $R^3$ and $R^4$ are connected together to be $C_4$–$C_6$ alkylene such as tetramethylene, pentamethylene and hexamethylene; $R^5$ and $R^6$ are the same or different, and each is hydrogen or $C_1$–$C_6$ alkyl such as methyl, ethyl, propyl and butyl; or the ends of $R^5$ and $R^6$ are connected together to be $C_4$–$C_6$ alkylene such as tetramethylene, pentamethylene and hexamethylene.

The compound of the present invention can be produced by reacting a compound of the formula:

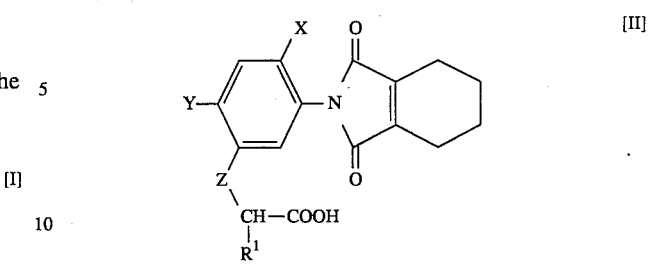

wherein X, Y, Z and $R^1$ are each as defined above, with an agent to produce acyl halide or an agent to produce an activated ester (reaction (i)), and reacting the resultant product with a compound of the formula:

wherein $R^3$ and $R^4$ are each as defined above, or a compound of the formula:

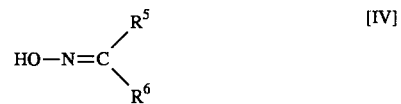

wherein $R^5$ and $R^6$ are each as defined above (reaction (ii)).

Examples of the agent to produce acyl halide used in reaction (i) are thionyl chloride, thionyl bromide, phosphorus trichloride, phosphorus tribromide, phosphorus pentachloride, phosphorus oxychloride, phosgene and oxalyl dichloride.

Examples of the agent to produce activated ester are N,N'-disubstituted carbodiimide such as N,N'-dicyclohexylcarbodiimide, N,N'-diisopropylcarbodiimide and 1-ethyl-3-(3-dimethylaminopropyl)carbodiimide hydrochloride, arylsulfonyl chloride such as 2,4,6-trimethylbenzenesulfonyl chloride and 2,4,6-triisopropylbenzenesulfonyl chloride, N,N'-carbonyl diimidazole, diphenylphosphoryl azide, N-ethoxycarbonyl-2-ethoxy-1,2-dihydroquinoline, N-ethyl-2'-hydroxybenzisoxazolium trifluoroborate and N-ethyl-5-phenylisoxazolium-3'-sulfonate.

In the reaction (i), there is produced a compound of the formula

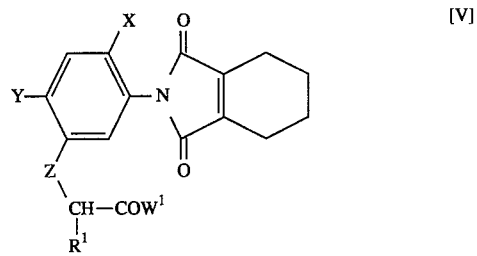

wherein X, Y, Z and $R^1$ are each as defined above; $W^1$ is halogen when the agent to produce acyl halide is used, or N,N'-disubstituted-2-isoureide when N,N'-disubstituted carbodiimide is used as the agent to produce an activated ester, or aryl sulfonyloxy when arylsulfonyl chloride is used, or imidazolyl when N,N'-carbonyldiimidazole is used, or azide when diphenylphosphorylazide is used, or ethoxycarbonyloxy when N-ethoxy-carbonyl-2-ethoxy-1,2-dihydroquinoline is used, or 3-(N-ethylaminocarbonyl)-2-hydroxyphenoxy when N-ethyl-2'-hydroxybenzisoxazolium trifluoroborate is used, or a group of the formula:

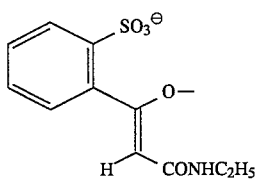

or a compound of the formula:

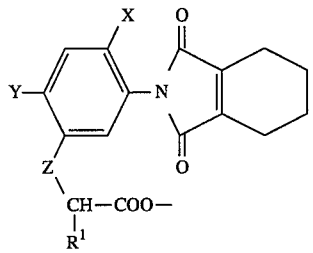

wherein X, Y, Z and $R^1$ are each as defined above when N-ethyl-5-phenylisoxazolium-3'-sulfonate is used.

The agent to produce an acyl halide or the agent to produce an activated ester and the compound [III] or [IV] are used in amounts of 1 to 10 equivalents and 1 to 5 equivalents, respectively, to one equivalent of the compound [II].

If necessary, the reactions (i) and (ii) may be carried out in the presence of a base. Examples of the base are organic bases such as 1-methylimidazole, 3-nitro-1H-1,2,4-triazole, 1H-tetrazole, 1H-1,2,4-triazole, imidazole, pyridine and triethylamine; and inorganic bases such as potassium carbonate. The base is used in an amount of 1 to 20 equivalents to one equivalent of the compound [II].

The reactions (i) and (ii) are usually carried out in an inert solvent. Examples of the solvent are aliphatic hydrocarbons such as hexane, heptane, ligroin and petroleum ether; aromatic hydrocarbons such as benzene, toluene and xylene; halogenated hydrocarbons such as chloroform, carbon tetrachloride, dichloroethane, chlorobenzene and dichlorobenzene; ethers such as diethyl ether, diisopropyl ether, dioxane, tetrahydrofuran and diethyleneglycol dimethyl ether; ketones such as acetone, methyl ethyl ketone, methyl isobutyl ketone, isophorone and cyclohexanone; esters such as ethyl formate, ethyl acetate and butyl acetate; nitro compounds such as nitroethane and nitrobenzene; nitriles such as acetonitrile and isobutyronitrile; tertiary amines such as pyridine, triethylamine, N,N-diethylaniline, tributylamine and N-methylmorpholine; acid amides such as N,N-dimethylformamide; sulfur compounds such as dimethyl sulfoxide and sulfolane; and a mixture thereof.

The reactions (i) and (ii) are usually carded out at a temperature of 0° C. to the boiling point of the solvent used for a period of a moment to 24 hours.

After completion of the reaction, the reaction mixture is subjected to an ordinary post-treatment. For example, water is added to the reaction mixture, and the resultant mixture is extracted with an organic solvent, followed by concentration. If necessary, any purification such as chromatography, distillation or recrystallization can be employed, thus obtaining the desired compound.

The compound [II] can be produced according to a method as described in U.S. Pat. No. 4,770,695 and 4,684,397.

Some of the compounds of the present invention which can be produced according to the production process described above are shown in Table 1.

TABLE 1

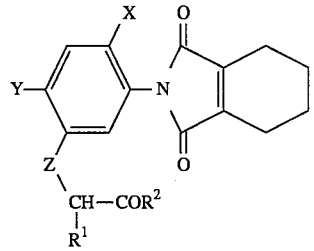

[I]

| Compound No. | X | Y | Z | $R^1$ | $R^2$ |
|---|---|---|---|---|---|
| 1 | F | Cl | O | H | O—N(CH₃)₂ |
| 2 | F | Cl | O | CH₃ | O—N(CH₃)₂ |
| 3 | F | Cl | O | C₂H₅ | O—N(CH₃)₂ |
| 4 | F | Cl | O | C₄H₉(n) | O—N(CH₃)₂ |
| 5 | F | Cl | S | H | O—N(CH₃)₂ |
| 6 | F | Cl | S | CH₃ | O—N(CH₃)₂ |
| 7 | F | Cl | S | C₂H₅ | O—N(CH₃)₂ |
| 8 | F | Cl | S | C₄H₉(n) | O—N(CH₃)₂ |
| 9 | F | Cl | O | H | O—NHCH₃ |
| 10 | F | Cl | O | H | O—NHC₃H₇(i) |
| 11 | F | Cl | O | H | O—NHC₄H₉(t) |
| 12 | F | Cl | O | H | O—NHC₆H₁₁(c) |
| 13 | F | Cl | O | H | O—N(CH₃)(C₂H₅) |
| 14 | F | Cl | O | H | O—N(C₂H₅)₂ |
| 15 | F | Cl | O | H | O—N(C₃H₇(n))₂ |
| 16 | F | Cl | O | H | O—N(C₄H₉(n))₂ |
| 17 | F | Cl | O | H | O—N(CH₂C₆H₅)₂ |
| 18 | F | Cl | O | H | O—N(tetramethylene) |
| 19 | F | Cl | O | H | O—N(pentamethylene) |
| 20 | F | Cl | O | H | O—N(hexamethylene) |
| 21 | F | Cl | O | CH₃ | O—NHCH₃ |
| 22 | F | Cl | O | CH₃ | O—NH₃C₃H₇(i) |
| 23 | F | Cl | O | CH₃ | O—NHC₄H₉(t) |
| 24 | F | Cl | O | CH₃ | O—NHC₆H₁₁(c) |
| 25 | F | Cl | O | CH₃ | O—N(CH₃)(C₂H₅) |
| 26 | F | Cl | O | CH₃ | O—N(C₂H₅)₂ |
| 27 | F | Cl | O | CH₃ | O—N(C₃H₇(n))₂ |
| 28 | F | Cl | O | CH₃ | O—N(C₄H₉(n))₂ |
| 29 | F | Cl | O | CH₃ | O—N(CH₂C₆H₅)₂ |
| 30 | F | Cl | O | CH₃ | O—N(tetramethylene) |
| 31 | F | Cl | O | CH₃ | O—N(pentamethylene) |
| 32 | F | Cl | O | CH₃ | O—N(hexamethylene) |
| 33 | F | Cl | S | H | O—NHCH₃ |
| 34 | F | Cl | S | H | O—NHC₃H₇(i) |
| 35 | F | Cl | S | H | O—NHC₄H₉(t) |
| 36 | F | Cl | S | H | O—NHC₆H₁₁(c) |
| 37 | F | Cl | S | H | O—N(CH₃)(C₂H₅) |
| 38 | F | Cl | S | H | O—N(C₂H₅)₂ |
| 39 | F | Cl | S | H | O—N(C₃H₇(n))₂ |
| 40 | F | Cl | S | H | O—N(C₄H₉(n))₂ |
| 41 | F | Cl | S | H | O—N(CH₂C₆H₅)₂ |
| 42 | F | Cl | S | H | O—N(tetramethylene) |
| 43 | F | Cl | S | H | O—N(pentamethylene) |
| 44 | F | Cl | S | H | O—N(hexamethylene) |
| 45 | F | Cl | S | CH₃ | O—NHCH₃ |
| 46 | F | Cl | S | CH₃ | O—NHC₃H₇(i) |
| 47 | F | Cl | S | CH₃ | O—NHC₄H₉(t) |
| 48 | F | Cl | S | CH₃ | O—NHC₆H₁₁(c) |
| 49 | F | Cl | S | CH₃ | O—N(CH₃)(C₂H₅) |
| 50 | F | Cl | S | CH₃ | O—N(C₂H₅)₂ |
| 51 | F | Cl | S | CH₃ | O—N(C₃H₇(n))₂ |
| 52 | F | Cl | S | CH₃ | O—N(C₄H₉(n))₂ |
| 53 | F | Cl | S | CH₃ | O—N(CH₂C₆H₅)₂ |
| 54 | F | Cl | S | CH₃ | O—N(tetramethylene) |
| 55 | F | Cl | S | CH₃ | O—N(pentamethylene) |
| 56 | F | Cl | S | CH₃ | O—N(hexamethylene) |
| 57 | F | F | O | H | O—N(CH₃)₂ |
| 58 | F | F | O | CH₃ | O—N(CH₃)₂ |
| 59 | F | F | S | H | O—N(CH₃)₂ |
| 60 | F | F | S | CH₃ | O—N(CH₃)₂ |

TABLE 1-continued

[Structure I: phenyl ring with X (ortho to N), Y (para to N via one position), Z–CH(R¹)–COR² substituent; N attached to tetrahydrophthalimide (cyclohexene-fused succinimide)]

| Compound No. | X | Y | Z | R¹ | R² |
|---|---|---|---|---|---|
| 61 | F | Br | O | H | O—N(CH₃)₂ |
| 62 | F | Br | O | CH₃ | O—N(CH₃)₂ |
| 63 | F | Br | S | H | O—N(CH₃)₂ |
| 64 | F | Br | S | CH₃ | O—N(CH₃)₂ |
| 65 | F | Cl | S | H | O—N=CHCH₃ |
| 66 | F | Cl | S | H | O—N=CHC₃H₇(i) |
| 67 | F | Cl | S | H | O—N=CHC₄H₉(t) |
| 68 | F | Cl | S | H | O—N=C(CH₃)₂ |
| 69 | F | Cl | S | H | O—N=C(CH₃)(C₂H₅) |
| 70 | F | Cl | S | H | O—N=C(C₂H₅)₂ |
| 71 | F | Cl | S | H | O—N=C(C₄H₉(n))₂ |
| 72 | F | Cl | S | H | O—N=C(tetramethylene) |
| 73 | F | Cl | S | H | O—N=C(pentamethylene) |
| 74 | F | Cl | S | H | O—N=C(hexamethylene) |
| 75 | F | Cl | S | CH₃ | O—N=CHCH₃ |
| 76 | F | Cl | S | CH₃ | O—N=CHC₃H₇(i) |
| 77 | F | Cl | S | CH₃ | O—N=CHC₄H₉(t) |
| 78 | F | Cl | S | CH₃ | O—N=C(CH₃)₂ |
| 79 | F | Cl | S | CH₃ | O—N=C(CH₃)(C₂H₅) |
| 80 | F | Cl | S | CH₃ | O—N=C(C₂H₅)₂ |
| 81 | F | Cl | S | CH₃ | O—N=C(C₄H₉(n))₂ |
| 82 | F | Cl | S | CH₃ | O—N=C(tetramethylene) |
| 83 | F | Cl | S | CH₃ | O—N=C(pentamethylene) |
| 84 | F | Cl | S | CH₃ | O—N=C(hexamethylene) |
| 85 | F | F | S | H | O—N=C(CH₃)₂ |
| 86 | F | F | S | CH₃ | O—N=C(CH₃)₂ |
| 87 | F | Br | S | H | O—N=C(CH₃)₂ |
| 88 | F | Br | S | CH₃ | O—N=C(CH₃)₂ |
| 89 | H | Cl | O | H | O—N(CH₃)₂ |
| 90 | H | Cl | O | CH₃ | O—N(CH₃)₂ |
| 91 | H | Cl | O | C₂H₅ | O—N(CH₃)₂ |
| 92 | H | Cl | O | C₄H₉(n) | O—N(CH₃)₂ |
| 93 | H | Cl | S | H | O—N(CH₃)₂ |
| 94 | H | Cl | S | CH₃ | O—N(CH₃)₂ |
| 95 | H | Cl | S | C₂H₅ | O—N(CH₃)₂ |
| 96 | H | Cl | S | C₄H₉(n) | O—N(CH₃)₂ |
| 97 | H | Cl | O | H | O—NHCH₃ |
| 98 | H | Cl | O | H | O—NHC₃H₇(i) |
| 99 | H | Cl | O | H | O—NHC₄H₉(t) |
| 100 | H | Cl | O | H | O—NHC₆H₁₁(c) |
| 101 | H | Cl | O | H | O—N(CH₃)(C₂H₅) |
| 102 | H | Cl | O | H | O—N(C₂H₅)₂ |
| 103 | H | Cl | O | H | O—N(C₃H₇(n))₂ |
| 104 | H | Cl | O | H | O—N(C₄H₉(n))₂ |
| 105 | H | Cl | O | H | O—N(CH₂C₆H₅)₂ |
| 106 | H | Cl | O | H | O—N(tetramethylene) |
| 107 | H | Cl | O | H | O—N(pentamethylene) |
| 108 | H | Cl | O | H | O—N(hexamethylene) |
| 109 | H | Cl | O | CH₃ | O—NHCH₃ |
| 110 | H | Cl | O | CH₃ | O—NHC₃H₇(i) |
| 111 | H | Cl | O | CH₃ | O—NHC₄H₉(t) |
| 112 | H | Cl | O | CH₃ | O—NHC₆H₁₁(c) |
| 113 | H | Cl | O | CH₃ | O—N(CH₃)(C₂H₅) |
| 114 | H | Cl | O | CH₃ | O—N(C₂H₅)₂ |
| 115 | H | Cl | O | CH₃ | O—N(C₃H₇(n))₂ |
| 116 | H | Cl | O | CH₃ | O—N(C₄H₉(n))₂ |
| 117 | H | Cl | O | CH₃ | O—N(CH₂C₆H₅)₂ |
| 118 | H | Cl | O | CH₃ | O—N(tetramethylene) |
| 119 | H | Cl | O | CH₃ | O—N(pentamethylene) |
| 120 | H | Cl | O | CH₃ | O—N(hexamethylene) |
| 121 | H | Cl | S | H | O—NHCH₃ |
| 122 | H | Cl | S | H | O—NHC₃H₇(i) |
| 123 | H | Cl | S | H | O—NHC₄H₉(t) |
| 124 | H | Cl | S | H | O—NHC₆H₁₁(c) |
| 125 | H | Cl | S | H | O—N(CH₃)(C₂H₅) |
| 126 | H | Cl | S | H | O—N(C₂H₅)₂ |
| 127 | H | Cl | S | H | O—N(C₃H₇(n))₂ |
| 128 | H | Cl | S | H | O—N(C₄H₉(n))₂ |
| 129 | H | Cl | S | H | O—N(CH₂C₆H₅)₂ |
| 130 | H | Cl | S | H | O—N(tetramethylene) |
| 131 | H | Cl | S | H | O—N(pentamethylene) |
| 132 | H | Cl | S | H | O—N(hexamethylene) |
| 133 | H | Cl | S | CH₃ | O—NHCH₃ |
| 134 | H | Cl | S | CH₃ | O—NHC₃H₇(i) |
| 135 | H | Cl | S | CH₃ | O—NHC₄H₉(t) |
| 136 | H | Cl | S | CH₃ | O—NHC₆H₁₁(c) |
| 137 | H | Cl | S | CH₃ | O—N(CH₃)(C₂H₅) |
| 138 | H | Cl | S | CH₃ | O—N(C₂H₅)₂ |
| 139 | H | Cl | S | CH₃ | O—N(C₃H₇(n))₂ |
| 140 | H | Cl | S | CH₃ | O—N(C₄H₉(n))₂ |
| 141 | H | Cl | S | CH₃ | O—N(CH₂C₆H₅)₂ |
| 142 | H | Cl | S | CH₃ | O—N(tetramethylene) |
| 143 | H | Cl | S | CH₃ | O—N(pentamethylene) |
| 144 | H | Cl | S | CH₃ | O—N(hexamethylene) |
| 145 | H | F | O | H | O—N(CH₃)₂ |
| 146 | H | F | O | CH₃ | O—N(CH₃)₂ |
| 147 | H | F | S | H | O—N(CH₃)₂ |
| 148 | H | F | S | CH₃ | O—N(CH₃)₂ |
| 149 | H | Br | O | H | O—N(CH₃)₂ |
| 150 | H | Br | O | CH₃ | O—N(CH₃)₂ |
| 151 | H | Br | S | H | O—N(CH₃)₂ |
| 152 | H | Br | S | CH₃ | O—N(CH₃)₂ |
| 153 | H | Cl | S | H | O—N=CHCH₃ |
| 154 | H | Cl | S | H | O—N=CHC₃H₇(i) |
| 155 | H | Cl | S | H | O—N=CHC₄H₉(t) |
| 156 | H | Cl | S | H | O—N=C(CH₃)₂ |
| 157 | H | Cl | S | H | O—N=C(CH₃)(C₂H₅) |
| 158 | H | Cl | S | H | O—N=C(C₂H₅)₂ |
| 159 | H | Cl | S | H | O—N=C(C₄H₉(n))₂ |
| 160 | H | Cl | S | H | O—N=C(tetramethylene) |
| 161 | H | Cl | S | H | O—N=C(pentamethylene) |
| 162 | H | Cl | S | H | O—N=C(hexamethylene) |
| 163 | H | Cl | S | CH₃ | O—N=CHCH₃ |
| 164 | H | Cl | S | CH₃ | O—N=CHC₃H₇(i) |
| 165 | H | Cl | S | CH₃ | O—N=CHC₄H₉(t) |
| 166 | H | Cl | S | CH₃ | O—N=C(CH₃)₂ |
| 167 | H | Cl | S | CH₃ | O—N=C(CH₃)(C₂H₅) |
| 168 | H | Cl | S | CH₃ | O—N=C(C₂H₅)₂ |
| 169 | H | O | S | CH₃ | O—N=C(C₄H₉(n))₂ |
| 170 | H | Cl | S | CH₃ | O—N=C(tetramethylene) |
| 171 | H | Cl | S | CH₃ | O—N=C(pentamethylene) |
| 172 | H | Cl | S | CH₃ | O—N=C(hexamethylene) |
| 173 | H | F | S | H | O—N=C(CH₃)₂ |
| 174 | H | F | S | CH₃ | O—N=C(CH₃)₂ |
| 175 | H | Br | S | H | O—N=C(CH₃)₂ |
| 176 | H | Br | S | CH₃ | O—N=C(CH₃)₂ |

In Table 1, the symbol "(c)" represents a cycloalkyl group, and the notations —N(tetramethylene), —N(pentamethylene), —N(hexamethylene), =C(tetramethylene), =C(pentamethylene) and =C(hexamethylene) represent TABLE 1-continued

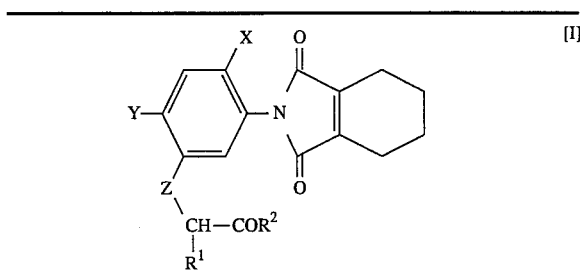

| Compound No. | X | Y | Z | R¹ | R² |
| --- | --- | --- | --- | --- | --- |

$-N\diagup\diagdown$ , $-N\diagup\diagdown$ , $-N\diagup\diagdown$ , $=C\diagup\diagdown$ , $=C\diagup\diagdown$ and $=C\diagup\diagdown$ , respectively.?

Some of the compounds of the present invention have optical isomers, which are also included within the scope of the present invention.

The compounds of the present invention have excellent herbicidal activity and some of them exhibit excellent selectivity between crop plants and weeds. That is, the compounds of the present invention have herbicidal activity against various unfavorable weeds as recited below under the foliar treatment or soil treatment on upland fields.

Polygonaceae:
 wild buckwheat (*Polygonum convolvulus*), pale smartweed (*Polygonum lapathifolium*), Pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)

Portulacaceae:
 common purslane (*Portulaca oleracea*)

Caryophyllaceae:
 common chickweed (*Stellaria media*)

Chenopodiaceae:
 common lambsquarters (*Chenopodium album*), kochia (*Kochia scoparia*)

Amaranthaceae:
 redroot pigweed (*Amaranthus retroflexus*), smooth pigweed (*Amaranthus hybridus*)

Crusiferae
 wild radish (*Raphanus raphanistrum*), wild mustard (*Sinapis arvensis*), shepherdspurse (*Capsella bursa-pastoris*)

Leguminosae:
 hemp sesbania (*Sesbania exaltata*), sicklepod (*Cassia obtusifolia*), Florida beggarweed (*Desmodium tortuosum*), white clover (*Trifolium repens*)

Malvaceae:
 velvetleaf(*Abutilon theophrasti*), prickly sida (*Sida spinosa*)

Violaceae:
 field pansy (*Viola arvensis*), wild pansy (*Viola tricolor*)

Rubiaceae:
 catchweed bedstraw (*cleavers*) (*Galium aparine*)

Convolvulaceae:
 ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*)

Labiatae:
 red deadnettle (*Lamium purpureum*), henbit (*Lamium amplexicaule*)

Solanaceae
 jimsonweed (*Datura stramonium*), black nightshade (*Solanum nigrum*)

Scrophulariaceae:
 birdseye speedwell (*Veronica persica*), ivyleaf speedwell (*Veronica hederaefolia*)

Compositae:
 common cocklebur (*Xanthium pensylvanicum*), common sunflower (*Helianthus annuus*), scentless chamomile (*Matricaria inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*)

Boraginaceae:
 field forget-me-not (*Myosotis arvensis*)

Asclepiadaceae:
 common milkweed (*Asclepias syriasa*)

Euphorbiaceae:
 sun spurge (*Euphorbia helioscopia*), spotted spurge (*Euphorbia maculata*)

Gramineae:
 barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annual*), blackgrass (*Alopecurus myosuroides*), wild oat (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*panicum texanum*), shattercane (*Sorghum vulgare*)

Commelinaceae
 common dayflower (*Commelina communis*),

Equisetaceae:
 field horsetail (*Equisetum arvense*)

Cyperaceae:
 rice flatsedge (*Cyperus iria*), purple nutsedge (*Cyperus rotundus*), yellow nutsedge (*Cyperus esculentus*)

Further, some of the compounds of the present invention have no problematic phytotoxicity on main crops such as corn (*Zea mays*), wheat (*Triticum aestivum*), barley (*Hordeum vulgare*), rice (*Oryza sativa*), sorghum (*Sorghum bicolor*), soybean (*Glycine max*), cotton (Gossypium spp.), sugar beet (*Beta vulgaris*), peanut (*Arachis hypogaea*), sunflower (*Helianthus annuus*), and canola (*Brassica napus*); and garden crops such as flowers and ornamental plants, and vegetables.

In addition, the compounds of the present invention can effectively control unfavorable weeds in the no-till cultivation. Further, some of them exhibit no problematic phytotoxicity on crop plants such as soybean, corn and wheat.

The compounds of the present invention also have herbicidal activity against various unfavorable weeds as recited below under the flooding treatment on paddy rice fields.

Gramineae:
   barnyardgrass (*Echinochloa oryzicola*)
Scrophulariaceae:
   common falsepimpernel (*Lindernia procurebens*)
Lythraceae:
   *Rotala indica, Ammannia multiflora*
Elatinaceae:
   *Elatine triandra*
Cyperaceae:
   smallflower umbrellaplant (*Cyperus difformis*), hardstem bulrush (*Scirpus juncoides*), needle spikerush (*Eleocharis acicularis*), *Cyperus serotinus, Eleocharis kuroguwai*
Pontederiaceae:
   *Monochoria vaginalis*
Alismataceae:
   *Sagittaria pygmaea, Sagittaria trifolia, Alisma canaliculatum*
Potamogetonaceae:
   roundleaf pondweed (*Potamogeton distinctus*)
Umbelliferae:
   *Oenanthe javanica*

Further, some of the compounds of the present invention also have no problematic phytotoxicity on transplanted paddy rice or directly-sown paddy rice.

Further, the compounds of the present invention can effectively control various unfavorable weeds in orchards, vineyards, plantations, grasslands, lawns or forests, or waterways, canals or other non-cultivated lands.

When the compound of the present invention is used as an active ingredient of herbicides, it is usually formulated with solid or liquid carders or diluents as well as surfactants and other auxiliary agents into conventional formulations such as emulsifiable concentrates, wettable powders, flowables, granules, concentrated emulsions, water-dispersible granules, concentrated emulsions, water-dispersible granules and solutions.

These formulations contain the compound of the present invention as an active ingredient at a content within the range of 0.001% to 80% by weight, preferably 0.003% to 70% by weight, based on the total weight of each of the formulations.

Examples of the solid carrier or diluent are fine powders or granules of mineral matters such as kaolin clay, attapulgite clay, bentonite, terra alba, pyrophyllite, talc, diatomaceous earth and calcite; organic substances such as walnut shell powder; water-soluble organic substances such as urea; inorganic salts such as ammonium sulfate; and synthetic hydrous silica. As the liquid carriers or diluent, there can be exemplified aromatic hydrocarbons such as alkylbenzenes (e.g., xylene), methylnaphthalene and phenylxylylethane; alcohols such as isopropanol, ethylene glycol and 2-ethoxyethanol; esters such as phthalic acid dialkyl esters; ketones such as acetone, cyclohexanone and isophorone; mineral oils such as machine oil; vegetable oils such as soybean oil and cotton seed oil; dimethylsulfoxide, N,N-dimethylformamide, acetonitrile, N-methylpyrrolidone, water and the like.

Examples of the surfactant used for emulsification, dispersing or spreading are those of the anionic type, such as alkylsulfates, alkylsulfonates, alkylarylsulfonates, dialkylsulfosuccinates and phosphates of polyoxyethylene alkylaryl ether; and those of the nonionic type, such as polyoxyethylene alkyl ethers, polyoxyethylene alkylaryl ethers, polyoxyethylenepolyoxypropylene block copolymers, sorbitan fatty acid esters and polyoxyethylene sorbitan fatty acid esters.

Examples of the auxiliary agent used for formulation are ligninsulfonates, alginates, polyvinyl alcohol, gum arabic, carboxymethyl cellulose (CMC) and isopropyl acid phosphate (PAP).

The compound of the present invention is usually formulated in any suitable formulation and used in the pre-emergence or post-emergence control of unfavorable weeds in upland fields and paddy fields. The soil treatment includes soil surface treatment and soil incorporation. The foliar treatment includes application over the plants and directed application to the weeds to keep any chemical off the crop foliage.

Further, the compound of the present invention may be used together with other herbicides to enhance its herbicidal activity. Moreover, it may also be used in admixture with insecticide, acaricides, nematocides, fungicides, plant growth regulators, fertilizers, soil improvers and the like.

When the compound of the present invention is used as an active ingredient of herbicides, the dosage thereof is usually in the range of from 0.1 to 8000 grams, preferably from 1 to 2000 grams, per hectare, although it may vary depending upon the prevailing weather conditions, formulation type employed, application timing, type of application, soil involved, crop and weed species, and the like. A designated amount of the compound formulated in the form of emulsifiable concentrates, wettable powders, flowables, concentrated emulsions, water-dispersible granules, solutions or the like, may usually be employed by diluting it with water at a volume of about 10 to 1000 liters per hectare, if necessary, with addition of an adjuvant such as a spreading agent. The compound formulated in the form of granules or some kinds of flowables or solutions may usually be applied without any dilution.

Examples of the adjuvant include, in addition to the surfactants as described above, polyoxyethylene resin acids (esters), ligninsulfonates, abietates, dinaphthyl methanedisulfonates, crop oil concentrates and crop oils such as soybean oil, corn oil, cotton seed oil and sunflower oil.

The compound of the present invention can also be used as an active ingredient of harvesting aids such as defoliants and desiccating agents for cotton and desiccating agents for potato (*Solanum tuberosum*). In that case, the compound of the present invention is usually formulated in the same manner as the case where it is used as an active ingredient of herbicides, and used alone or in admixture with other harvesting aids before the crops are harvested.

The present invention will be further illustrated by way of the following production examples, formulation examples and test examples, which are not to be construed to limit the scope thereof. The compounds of the present invention are designated by the corresponding numbers as shown in Table 1.

PRODUCTION EXAMPLE 1:

Preparation of Compound 38

In 20 ml of tetrahydrofuran, 1.85 g of 2-(5-carboxymethylthio-4-chloro -2-fluorophenyl)- 4,5,6,7-tetrahydro-2H-isoindole-1,3-dione was dissolved, to which 0.97 g of N,N'-carbonyldiimidazole was added and the resultant mixture was stirred for 30 minutes at room temperature. To the resultant mixture, 0.53 g of N,N-diethylhydroxylamine was added, and the resultant mixture was stirred for 2 hours at room temperature. After completion of the reaction, the reaction mixture was poured into a saturated saline solution and extracted with ethyl acetate. The extract was washed with a saturated saline solution, dried with anhydrous magnesium sulfate, and evaporated to remove the solvent under reduced pressure. The residue was purified by silica gel chromatography (eluent; hexane:ethyl acetate=5:1 to 3:1), which afforded 1.60 g of 2-[5-(N,N-diethylaminooxycarbonylmethylthio)-4-chloro-2-fluorophenyl]-4,5,6,7-tetrahydro- 2H-isoindole-1,3-dione.

$^1$H-NMR [60 MHz, CDCl$_3$] δ ppm: 1.04 (6H, t, J=6.6 Hz), 1.64–2.05 (4H, m), 2.16–2.63 (4H, m), 2.86 (4H, q, J=6.6 Hz), 3.62 (2H, s), 7.28 (1H, d, J=18.0 Hz), 7.31 (1H, s).

SOME COMPOUNDS OF THE PRESENT INVENTION WERE PRODUCED ACCORDING TO PRODUCTION EXAMPLE 1.

Compound 5: $^1$H-NMR [60 MHz, CDCl$_3$] δ ppm: 1.59–2.01 (4H, m), 2.11–2.59 (4H, m), 2.61 (6H, s), 3.50 (2H, s), 7.14 (1H, d, J=15.0 Hz), 7.16 (1H, s).

Compound 6: $^1$H-NMR [60 MHz, CDCl$_3$] δ ppm: 1.55 (3H, d, J=7 Hz), 1.65–2.05 (4H, m); 2.25–2.60 (4H, m), 2.62 (6H, s), 3.80 (1H, q, J=7 Hz), 7.25 (1H, d, J=10 Hz), 7.42 (1H, d, J=7 Hz).

Compound 14: $^1$H-NMR [60 MHz, CDCl$_3$] δ ppm: 1.10 (6H, t, J=7 Hz), 1.60–2.0 (4H, m), 2.20–2.60 (4H, m), 2.90 (4H, q, J=7 Hz), 4.70 (2H, s), 6.80 (1H, d, J=6 Hz), 7.25 (1H, d, J=9 Hz).

Compound 26: m.p., 85°–86° C.

Compound 36: m.p., 105.4° C.

Compound 41: m.p., 120.9° C.

Compound 78: $^1$H-NMR [60 MHz, CDCl$_3$] δ ppm: 1.57 (3H, d, J=6 Hz), 1.60–2.00 (4H, m), 2.00 (6H, s), 2.20–2.60 (4H, m), 4.00 (1H, q, J=6 Hz), 7.32 (1H, d, J=10 Hz), 7.47 (1H, d, J=6 Hz).

The following will describe formulation examples wherein parts are by weight. The compounds of the present invention are designated by the corresponding numbers as shown in Table 1.

FORMULATION EXAMPLE 1

Fifty parts of any one of the compounds 5, 6, 14, 26, 36, 38, 41, 44, 51 and 78, 3 parts of calcium lignin sulfonate, 2 parts of sodium laurylsulfate and 45 parts of synthetic hydrous silicate are well mixed while being powdered to obtain a wettable powder.

FORMULATION EXAMPLE 2

Ten parts of any one of the compounds 5, 6, 14, 26, 36, 38, 41, 44, 51 and 78, 14 parts of polyoxyethylene styryl phenyl ether, 6 parts of calcium dodecylbenzenesulfonate, 35 parts of xylene, and 35 parts of cyclohexanone are well mixed to obtain an emulsifiable concentrate.

FORMULATION EXAMPLE 3

Two parts of any one of the compounds 5, 6, 14, 26, 36, 38, 41, 44, 51 and 78, 2 parts of synthetic hydrous silicate, 2 parts of calcium ligninsulfonate, 30 parts of bentonite and 64 parts of kaolin clay are well mixed while being powdered. The mixture is then kneaded with water, granulated and dried to obtain granules.

FORMULATION EXAMPLE 4

Twenty five parts of any one of the compounds 5, 26, 36 and 38, 50 parts a of 10% solution of polyvinyl alcohol and 25 parts of water are well mixed, and the mixture was then pulverized until the particle size thereof becomes not greater than 5 microns to obtain a flowable material.

The following will describe test examples. The compounds of the present invention are designated by the corresponding numbers as shown in Table 1.

The herbicidal activity on weeds and the phytotoxicity to crop plants were determined by visual observation as to the degree of germination and growth of the test plants (i.e., weeds and crop plants), and rated with an index 0, 1, 2, 3, 4 or 5, the numeral "0" indicating little or no difference as seen in comparison with the untreated plants and the numeral "5" indicating the complete death of the test plants or the complete inhibition of their germination or growth. The numeral "0", "1", "2" or "3" shows that the herbicidal effect is insufficient.

TEST EXAMPLE 1

Cylindrical plastic pots (diameter, 10 cm; height, 10 cm) were filled with upland field soil, and the seeds of velvetleaf were sowed therein and covered with soil. The test compound formulated in the emulsifiable concentrate according to Formulation Example 2 was diluted with water, and the dilution was sprayed onto the soil surface by a sprayer at an application amount of 1000 liters per hectare. The test plants were grown in a greenhouse for 19 days, and the herbicidal activity was examined. The results are shown in Table 2.

TABLE 2

| Compound No. | Dosage (g/ha) | Herbicidal activity Velvetleaf |
|---|---|---|
| 5 | 500 | 5 |
| 6 | 500 | 5 |
| 14 | 500 | 5 |
| 26 | 500 | 5 |
| 36 | 500 | 5 |
| 38 | 500 | 5 |
| 41 | 500 | 5 |
| 44 | 500 | 4 |
| 51 | 500 | 5 |
| 78 | 500 | 5 |

TEST EXAMPLE 2

Cylindrical plastic pots (diameter, 10 cm; height, 10 cm) were filled with upland field soil, and seeds of tall morningglory and velvetleaf were sowed therein and cultivated in a greenhouse for 7 days. After that, the test compound formulated in the emulsifiable concentrate according to Formulation Example 2 was diluted with water containing a spreading agent, and the dilution was sprayed over the foliage of the test plants by a sprayer at an application amount of 1000 liters per hectare. After the treatment, the test plants were further grown in the greenhouse for 19 days, and the herbicidal activity was examined. The results are shown in Table 3.

TABLE 3

| Compound No. | Dosage (g/ha) | Herbicidal activity Tall morningglory | Velvetleaf |
|---|---|---|---|
| 5 | 31 | 5 | 5 |
| 6 | 31 | 5 | 5 |
| 14 | 31 | 5 | 5 |
| 26 | 31 | 5 | 5 |
| 36 | 31 | 5 | 5 |
| 38 | 31 | 5 | 5 |
| 41 | 31 | 5 | 5 |

TABLE 3-continued

| Compound No. | Dosage (g/ha) | Herbicidal activity | |
|---|---|---|---|
| | | Tall morningglory | Velvetleaf |
| 44 | 31 | 5 | 5 |
| 51 | 31 | 5 | 5 |
| 78 | 31 | 5 | 5 |

What is claimed is:

1. A compound of the formula:

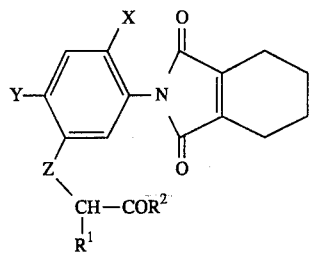
(I)

wherein X is hydrogen or halogen; Y is halogen; Z is oxygen or sulfur; $R^1$ is hydrogen or alkyl; and $R^2$ is a group of the formula:

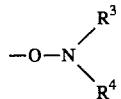

wherein $R^3$ and $R^4$ are the same or different, and each is hydrogen, alkyl, cycloalkyl or benzyl, or $R^3$ and $R^4$ may combine to form an alkylene group.

2. A compound according to claim 1, wherein Z is oxygen.

3. A compound according to claim 1, wherein Z is sulfur and $R^2$ is a group of the formula:

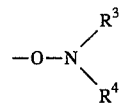

wherein $R^3$ and $R^4$ are each as defined in claim 1.

4. A compound according to claim 1, wherein $R^3$ and $R^4$ combine to form a tetramethylene, pentamethylene or hexamethylene group.

5. A compound according to claim 2, wherein $R^3$ and $R^4$ combine to form a tetramethylene, pentamethylene or hexamethylene group.

6. A herbicidal composition which comprises as an active ingredient a herbicidally effective amount of the compound according to claim 1, and an inert carrier or diluent.

7. A method for exterminating harmful weeds, which comprises applying a herbicidally effective amount of the compound according to claim 1 and an inert carrier or diluent to an area where the harmful weeds grow or would grow.

* * * * *